(12) United States Patent
Tang et al.

(10) Patent No.: US 12,091,654 B2
(45) Date of Patent: Sep. 17, 2024

(54) ELECTROPORATION APPARATUSES AND THEIR METHOD OF USE

(71) Applicants: Emily Chen Tang, Warren, NJ (US); Bryan Michael Gerber, Warren, NJ (US); Chadwick Phillip Pearson, Warren, NJ (US); Harsimran Panesar, Stirling, NJ (US)

(72) Inventors: Emily Chen Tang, Warren, NJ (US); Bryan Michael Gerber, Warren, NJ (US); Chadwick Phillip Pearson, Warren, NJ (US); Harsimran Panesar, Stirling, NJ (US)

(*) Notice: Subject to any disclaimer, the term of this patent is extended or adjusted under 35 U.S.C. 154(b) by 185 days.

(21) Appl. No.: 17/579,701

(22) Filed: Jan. 20, 2022

(65) Prior Publication Data

US 2022/0133922 A1 May 5, 2022

Related U.S. Application Data

(62) Division of application No. 14/679,327, filed on Apr. 6, 2015, now Pat. No. 11,260,137.

(60) Provisional application No. 61/975,828, filed on Apr. 6, 2014.

(51) Int. Cl.
| | |
|---|---|
| *C12N 13/00* | (2006.01) |
| *A23L 3/32* | (2006.01) |
| *A61L 2/08* | (2006.01) |
| *B08B 6/00* | (2006.01) |

(52) U.S. Cl.
CPC ............ *C12N 13/00* (2013.01); *A23L 3/32* (2013.01); *A61L 2/08* (2013.01); *B08B 6/00* (2013.01)

(58) Field of Classification Search
None
See application file for complete search history.

(56) References Cited

U.S. PATENT DOCUMENTS

2013/0041238 A1* 2/2013 Joseph .................. A61L 29/04
600/323

OTHER PUBLICATIONS

K.O. Andresen, et al., "Injection molded chips with integrated conducting polymer electrodes for electroporation of cells", Journal of Micromechanics and Microengineering, 20(5): paper No. 055010, 9 pages, April (Year: 2010).*

* cited by examiner

*Primary Examiner* — J. Christopher Ball
(74) *Attorney, Agent, or Firm* — Gearhart Law, LLC

(57) ABSTRACT

The device uses pulsed electric fields to prevent the growth of biofilm and the attachment of bacteria to targeted surfaces. The device sets up an electric field around or surrounding the surface itself. These pulsed electric fields disrupt biofilm formation and bacterial attachment to surfaces. The device is meant to prevent the formation of biofilm or attachment of bacteria to a surface as opposed to disinfecting the surface.

13 Claims, 11 Drawing Sheets

ELECTROPORATION APPARATUSES AND THEIR METHOD OF USE

CLAIM OF PRIORITY

This application is a Divisional of U.S. non-provisional application Ser. No. 14/679,327 filed Apr. 6, 2015, which claims priority to Provisional Patent Application Ser. No. 61/975,828 filed on Apr. 6, 2014, the contents of which are incorporated by reference herein in their entirety.

FIELD OF THE EMBODIMENTS

The present invention and its embodiments relate to the use of pulsed electric fields. In particular, the present invention relates to using pulsed electric fields to cause electroporation in various biofilms and/or prevent surface bacterial contamination.

BACKGROUND OF THE EMBODIMENTS

Biofilm is a collection of microbial cells that are a tightly bound matrix of primarily polysaccharide material, proteins, and DNA. These biofilms frequently exhibit strong bonding properties, and are incapable of being removed through gentle rinsing. One common problem in industries such as food processing is the buildup of biofilm and attachment of organisms to certain surfaces. For example, this buildup frequently occurs within the various tubes used throughout the food processing industry.

The prior art contemplates various methods for removing biofilm. However, many of the standard methods used in many food-processing industries today, such as alkali-based as well as acid-based cleaners, are capable of adequately removing extracellular polymeric biofilm matrix only when the correct process parameters (e.g. formulations, concentrations, time, temperature) are applied. The removal of biofilm and its attached bacteria can be facilitated through the use of mechanical force to the surface during cleaning. Common examples of these applications of mechanical force are brushing and scrubbing. The mechanical removal of biofilm and attached bacteria can be achieved via high-pressure spray hoses, however, these hoses cause the dispersion of bacteria over a wide area, which often results in the growth of mold and bacteria. Further, the interior of certain surfaces, such as tubing, is not readily accessible to be cleaned via mechanical force. Note that all of the above-mentioned techniques are all methods of treatment, as opposed to methods of prevention.

In contrast, the present invention employs the use of Pulsed Electric Fields (hereinafter "PEF"). PEF's are high intensity electric fields which are capable of disrupting a number of bacterial functions. Generally, PEF's are created by a power supply creating a difference in the electrical potential between two objects. Frequently, this difference is generated between two electrodes. However, this difference can be between a single electrode and another object. For example, this secondary object can be the earth, or the contents of someone's mouth. One way that PEF's are used to prevent the formation of biofilms is by causing electroporation in a wide variety of bacteria. Electroporation is the process of PEF's (or some other kind of electric field) causing small holes to form in the membrane of a given bacterium. Electroporation leads to decreased cell viability and proliferation in many different bacteria. Another way in which PEF's may be used to prevent the formation of biofilms is by affecting the surface properties of a cell. Chief amongst these properties are the cell's surface hydrophobicity, the extracellular polymers of the cell, and the electrostatic charge of the cell's surface. It has been shown that the application of a direct electrical current (which PEF's may induce) affects these properties of a cell such that the prevention of the growth of biofilm will be achieved.

One beneficial use of PEF's is in the food processing industry. There, PEF's are often used as an alternative to other pasteurization methods, due to the minimal heat generated when exposing a food stuff to a PEF. This has the benefit of limiting thermal degradation, a serious problem in the food processing industry. The prior art contains a few systems which do use PEF, albeit as a disinfectant. However, these systems must employ the use of a small chamber due to the fact that electric field is reduced as the distance between electrodes is increased. Further, these systems are difficult to scale up, and frequently must employ a vacuum system to prevent air bubbles from causing a fire hazard.

Another beneficial use of PEF's is in the removal of dental plaque. Previously a number of different devices have been used to remove dental plaque. A review of the previous solutions to removing dental plaque is provided:

Toothbrush: Over the years the brush head shape, filament shape and filament insertion method into the handle have changed in order to be most effective and comfortable. However, a detriment of all existing toothbrushes is that they need to be replaced every 3 or 4 months to be effective at cleaning one's mouth, due to the deterioration of the toothbrushes' bristles. Further, the head of a toothbrush can become infested with bacteria, greatly diminishing the cleaning effects of said toothbrush. Further, even when the brush head is appropriately maintained, according to P&G Oral Health, only a mere 65.1% of the plaque is removed by a manual brush.

Electric toothbrush: Electric toothbrushes are widely used because of their convenience, but the electric motors that power them may produce electromagnetic waves. It has been shown that electric toothbrushes generate low frequency magnetic fields (1-2000 Hz) which induce an electric current in dental appliances such as orthodontic and prosthetic appliances and dental implants. This can cause micro-discharges which can cause pain or change the properties of the implants. Further, accordingly to P&G Oral Health, only 73.6% of the plaque is removed by an electrical toothbrush.

Ultrasonic toothbrush: Device used to remove plaque, from teeth. Comprises of a toothbrush having a hollow, cylindrical handle that holds an electrical motor and is power by batteries (DC). The electrical motor (transducer) generates high frequency (above 20 kHz) mechanical waves along the brush. The ideal frequency of the ultrasonic pressure waves is between 0.75 MHZ and 1.6 MHZ, but it can range from 20 kHz to above 2000 kHz depending on the selection of materials utilized in the toothbrush and the components in the dentifrice to maximize cavitation and acoustic streaming in the fluids of the oral cavity. Maximum level of ultrasound energy coupled to the fluids within the oral cavity and to the teeth and gums and periodontal pockets, achieving maximum loosening of soft plaque. This technology has also been applied to dental scalar, however because of the high energy flow the scalars (and the toothbrushes) can heat up. Such devices can be uncomfortable because of the high intensity vibrations and high pitched audible sounds.

Dental floss: To remove interproximal plaque, dental floss is a very popular tool. However, achieving proper flossing technique can be difficult, resulting in this technique being less than universal in its application. Despite this, the American Dental Association (ADA) even reports that up to 80% of plaque may be removed by this method. However, a study aimed to assess systematically the use of dental floss in addition to the use of a tooth brush, as opposed to the effect of the use of a toothbrush alone on interproximal plaque and gingivitis, found that the use of dental floss provides no benefit. A subsequent study found that flossing was only effective in reducing interproximal caries risk when applied professionally. Their systematic review showed that high-quality professional flossing performed in first grade children on school days reduced caries risk by 40%. Self-flossing, on the contrary, failed to have the same beneficial effect.

Dental Scaler: A dental scaler is a hand-held device that has a metallic end shaped like a hook or curved blade and can be ultrasonic. To use the scaler, a user scrapes the long edge of the scaler's blade along each tooth's surface, from just above or below the gum line toward the end of the tooth. However, this is not something that should be done daily, since daily, consistent scraping can damage the enamel on the teeth (which does not regenerate), scratch implants, as well as inflict damage to a patient's gums. All of these scratches lead to a patient's teeth permanently having an increased surface area; giving bacteria a wider array of surfaces to grow on.

As has been shown above, the solutions in the prior art have a number of inadequacies with regard to the effectiveness of the treatment. None of the art described above addresses all of the issues that the present invention does.

SUMMARY OF THE EMBODIMENTS

The present invention provides for an electric field generator, comprising: a power source, having an output; a first electrode connected to said output of said power source and a ground. The first electrode and said ground are situated such that an electric field is generated in the space between said first electrode and the ground and the electric field has an intensity ranging from about 5V/cm to about 20 kV/cm. The ground may be comprised of an electrode with an opposite voltage of the first electrode, at least a plurality of electrodes, or a second electrode with an electric potential that differs from the first electrode. In an alternative embodiment, this electrical device generates an electric field with an intensity ranging from about 5V/cm and about 2000V/cm, preferably about 400V/cm to about 2000V/cm. In alternative embodiments, this electrical device can be incorporated into tooth brushes, dental trays, soda dispenser machines, and many other, not specifically enumerated devices.

The present invention also contemplates a method of inhibiting biofilm growth on a substrate, comprising the steps of: coating, said substrate with a conductive polymer; generating, a pulsed electric field with an intensity of at least 400V/cm; exposing, for a period of time, said substrate to said electric field. The period of time may be at least one second. The present invention also contemplates a method of preventing the formation of a biofilm, comprising: generating, an electric field from a power source capable of generating alternating current, where the power source is in electronic communication with a plurality of electrodes and exposing the at least one cell to said electric field. The at least one cell may be exposed to the electric field for at least one second. The at least one cell may be exposed to said electrical field for at least one pulse. The electric field may have an intensity ranging from about 5V/cm to about 2000V/cm or an intensity ranging from about 0.1 kV/cm to about 20 kV/cm. The at least one cell may be a bacterial cell which is located in solid or semi-solid food or is located in a liquid consumable.

The present invention also contemplates a method of causing electroporation in at least one cell, comprising: generating, an electric field from a power source generating alternating current operatively attached to a plurality of electrodes; exposing, said at least one cell to said electric field. These cells can be that of bacteria, fungi, or that of plant cells.

The current invention uses Pulsed Electric Fields (PEF) technology to prevent biofilm growth and bacterial attachment to surfaces. PEF are used to disrupt cell communication and cell attachment and therefore disrupt bacterial attachment and biofilm formation. This is different from the current use of high intensity PEF for disinfection. This invention uses lower intensity electric fields and less power than required for disinfection, to prevent bacterial attachment to surfaces. The electric fields used in this invention have the strength in the range of about 0.1 kV/cm to about 20 kV/cm and a medium frequency range of about 5 kHZ to about 50 kHz.

The application of PEF in this invention involves the use of fully insulated electrodes, which can be applied externally to devices and surfaces, ex. inside surfaces of closed tubing in food processing plants, medical equipment, medical tubing, implants, dental implants, or teeth. The high voltage insulation around the electrodes prevents current (except a minimal, <microAmp range leakage current) resulting in low power use. The mid-frequency range results in low radiation emission. As a result the invention can be scaled up to a large size without large power inputs. It can be used with existing equipment or built-in during manufacturing and easily incorporated into existing systems.

The prevention of biofilm formation saves the time and money spent to clean surfaces. Since the aim is prevention, as opposed to disinfection, many of the limitations of previous PEF systems do not apply. The present invention can be made to any size considering the dimensions of the surface (that has the PEF applied to it) can be varied. Therefore the present invention and its embodiments can be easily incorporated into existing systems. Referring back to the sample application in the food industry, some of the limitations are avoided. Where there previously was a small PEF treatment chamber set-up (which was previously needed to minimize electrode separation distance) can be eliminated. The electrodes in the present invention can be further apart due to the fact that weaker electric fields are needed. Also due to the larger electrode separation distance the presence of bubbles is not as detrimental. These are just sample limitations that can be avoided if the present invention was applied in one of its possible fields, the food industry.

Regarding PEF's use in removing dental plaque, the electric field changes the bacteria formation and thus naturally decreases the bacterial growth rate. This gentle cleaning approach reaches places that cannot be reached, and ensures the whole mouth gets cleaned. The present invention is used just like a normal toothbrush along with toothpaste but has a more long-term, preventative effect on plaque formation. Further, this embodiment of the present invention has the additional benefit of preventing biofilms from forming on the filaments of the toothbrush. The present invention does not take place of your daily oral hygiene routine. A person still needs to brush and floss regularly, but the present invention enhances daily cleaning. The present invention does not depend on current to affect the bacteria, since the current out is minimal, close to zero. Rather, the present invention uses the electric field which uses voltage and high frequency to out force on the bacteria changes and disrupting its physiology. Also, due to the ability of PEF's to remove dental plaque, the present invention is of particular use for cleaning dentures.

DESCRIPTION OF THE PREFERRED EMBODIMENTS

Figure 1:
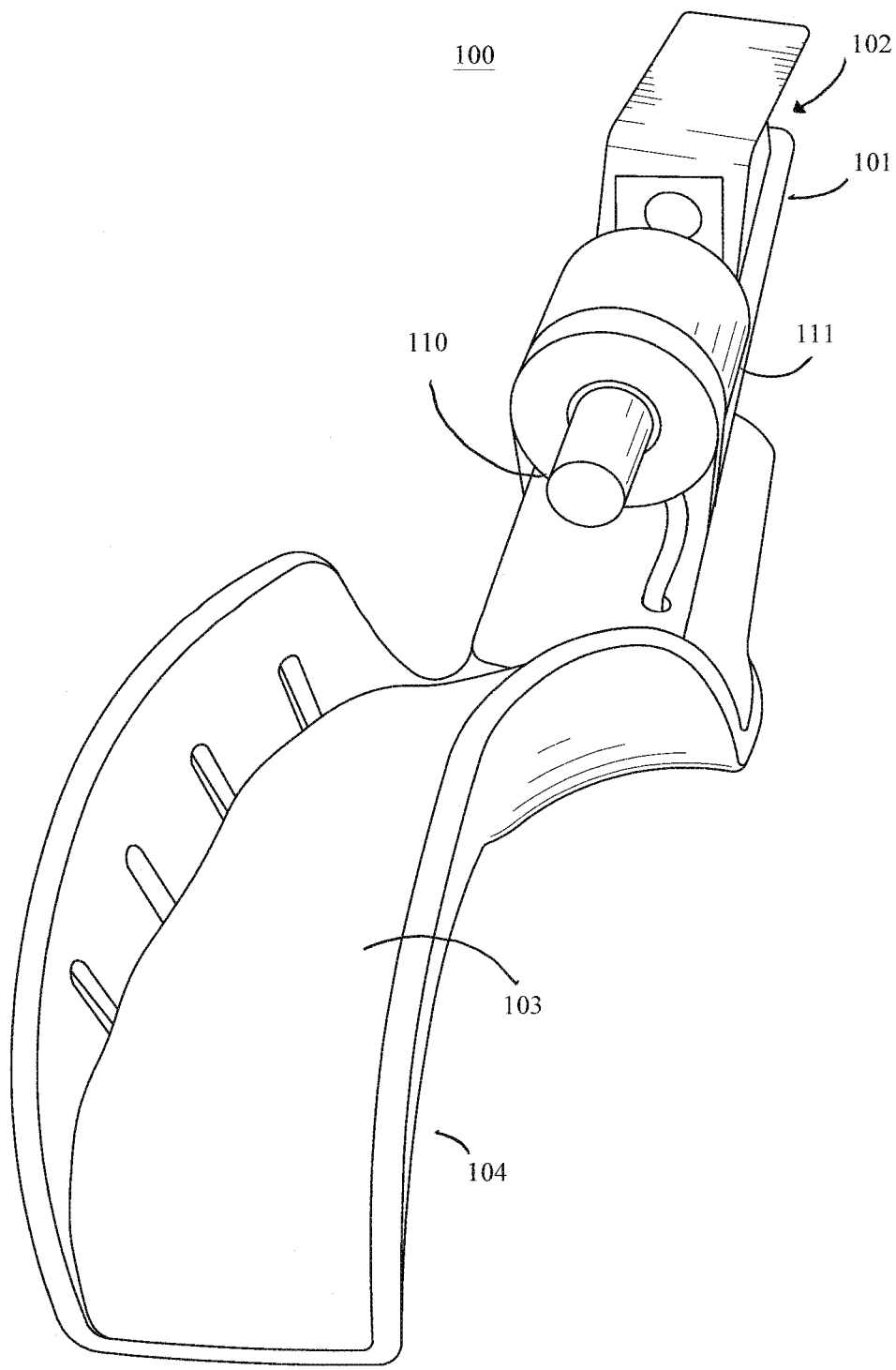
FIG. 1 is a front perspective view of an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring to FIG. 1, a front perspective view of an embodiment of the present invention is provided for. Here, electrical device 100 is incorporated into a dental tray. This embodiment is comprised of power supply 101, insulation 103, dental tray 104, transformer 111, plastic holder of coils in transformer 110, and electrode 108 (See FIG. 4). This embodiment may be used to clean the inside of a user's mouth when a user inserts dental tray 104 into their mouth and activates electrical device 100. This embodiment may also be used to clean dentures or other artificial teeth by resting those products on dental tray 104 and activating electrical device 100 via power supply 101.

In this and other embodiments, the transformer 111 may be capable of producing high and low voltage outputs as well as high and low frequency outputs. The plastic holder for the coils in the transformer 110 may comprise any number and combination of materials other than plastics or may be a combination of plastic types. Also equipped in this embodiment is AC adapter 102. In a preferred embodiment, power supply 101 is located in close proximity to AC adapter 102. In another preferred embodiment, power supply 101 and AC adapter 102 are one and the same. Insulation 103 is used to cover up electrode 108. Note that due to the nature of pulsed electric fields, as well as the nature of this particular embodiment, electrode 108 must be completed insulated. This provides for safety for the user as well as increased efficiency in generating said electric field. In this regard, insulation 103 may be comprised of a single piece that envelops electrode 108 or may be comprised of two pieces; one on top of electrode 108 and one below electrode 108, forming a seal where the two pieces meet.

While this particular embodiment of electrical device 100 is equipped with AC adapter 102, this disclosure contemplates an embodiment that is powered solely by DC power. In that embodiment, there is no need for AC adapter 102. In this particular embodiment the total length of the device will be around 19 cm. Where the cylindrical, insulated cover 105 is about 13 cm with about a 2 cm diameter and houses the power supply 101 and the AC connection 102 comes out from the back. Further, the mouth piece 104 length is about 6 cm and width is about 1.5 cm. However, this size varies based on the user's mouth and or denture size.

Figure 2:
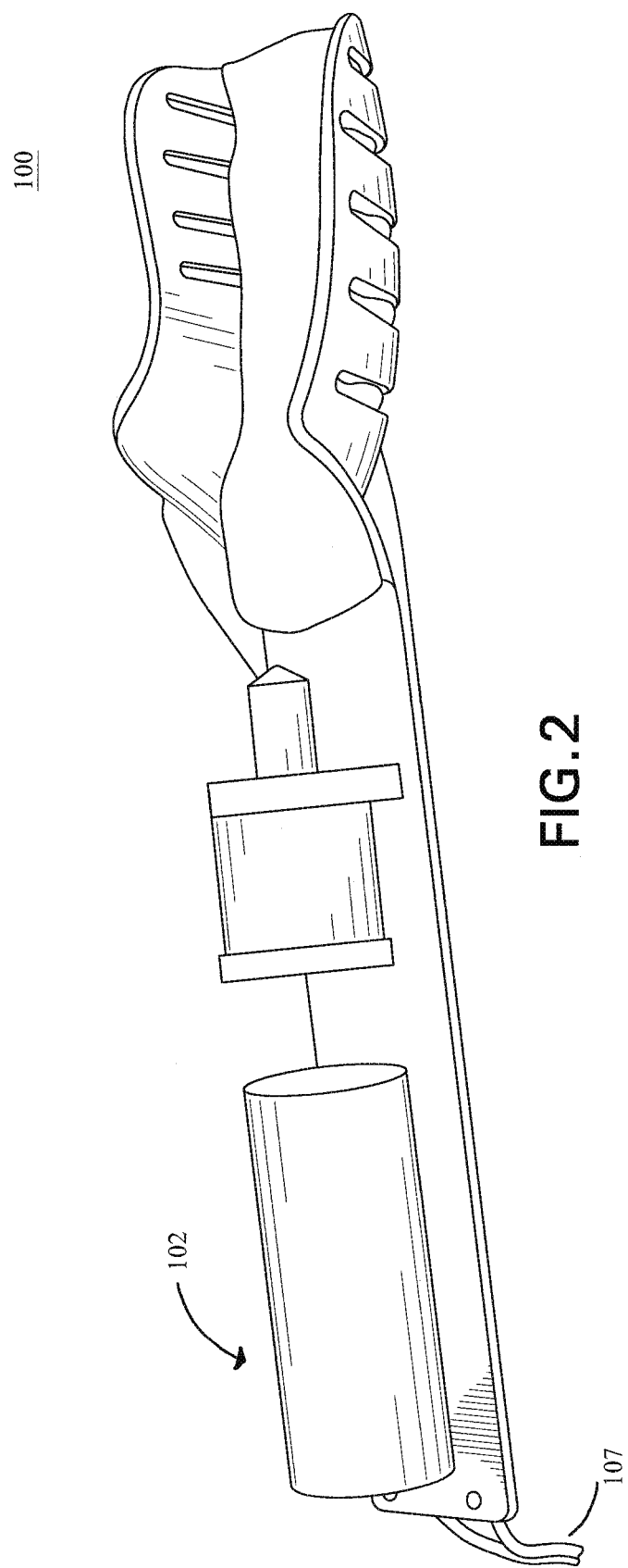
FIG. 2 is a side view of an embodiment of the present invention.

Turning to FIG. 2, is a side view of an embodiment of the present invention is provided for. While this embodiment is substantially similar to that embodiment shown in FIG. 1, this embodiment is equipped with the optional AC adapter output 107. When electrical device 100 is equipped with AC adapter 102, it is preferably equipped with AC adapter output 107. Note that, as previously mentioned, electrical device 100 may be operated solely via direct current, but it may also be operated with alternating current as well, if equipped with AC adapter 102 and AC adapter output 107.

Figure 3:
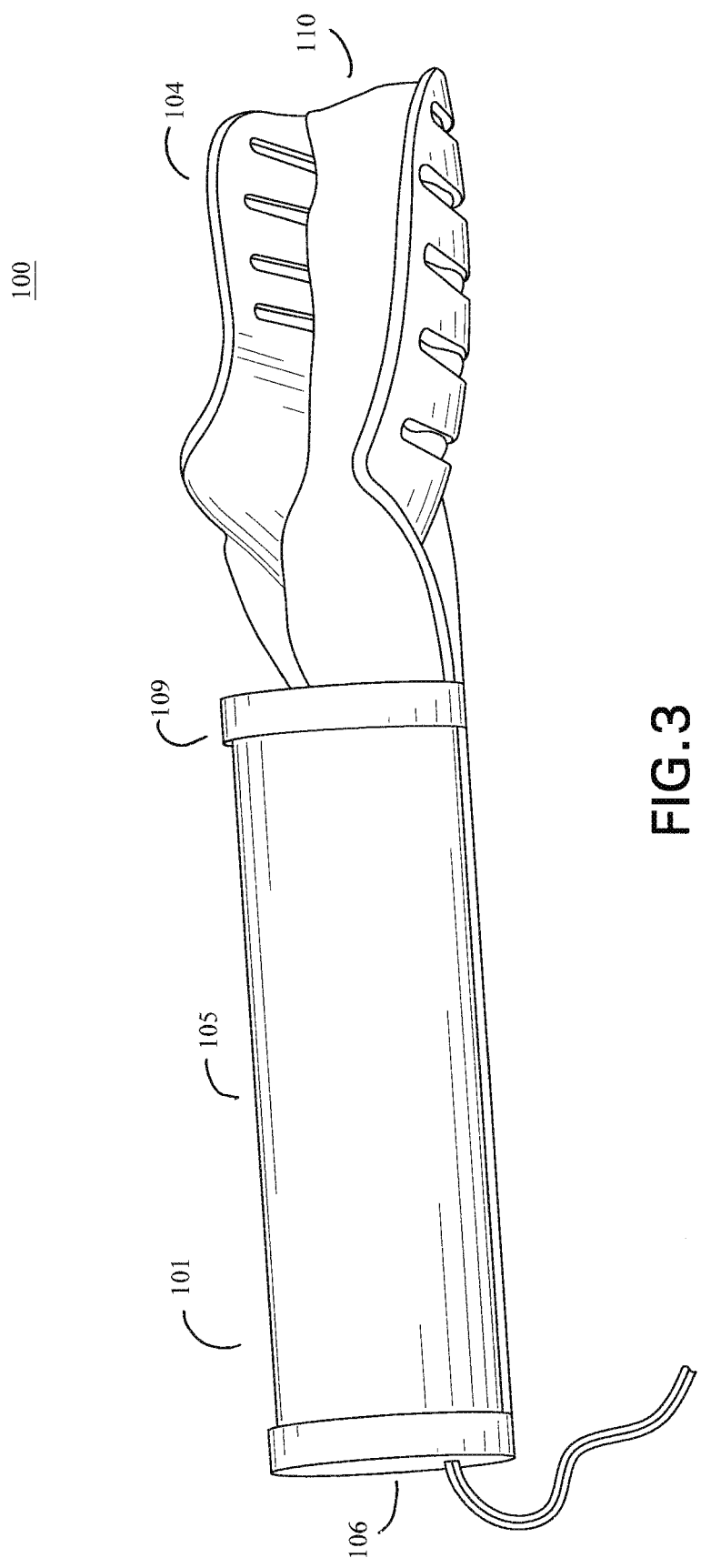
FIG. 3 is an alternative side view of an embodiment of the present invention.

FIG. 3 shows an alternative side view of an embodiment of the present invention. Here, electrical device 100 is still equipped with power supply 101, plastic holder of coils in transformer 110, and transformer 111 (See FIG. 1), optionally equipped AC adapter 102 and AC adapter output 107 (See FIG. 2), insulation 103, and dental tray 104. In addition to those components, this view shows insulated lid 106, insulated cover 105, and lid 109. These additional components provide for complete insulation of power supply 101 and plastic holder of coils in transformer 110, allowing for greater user safety.

Figure 4:
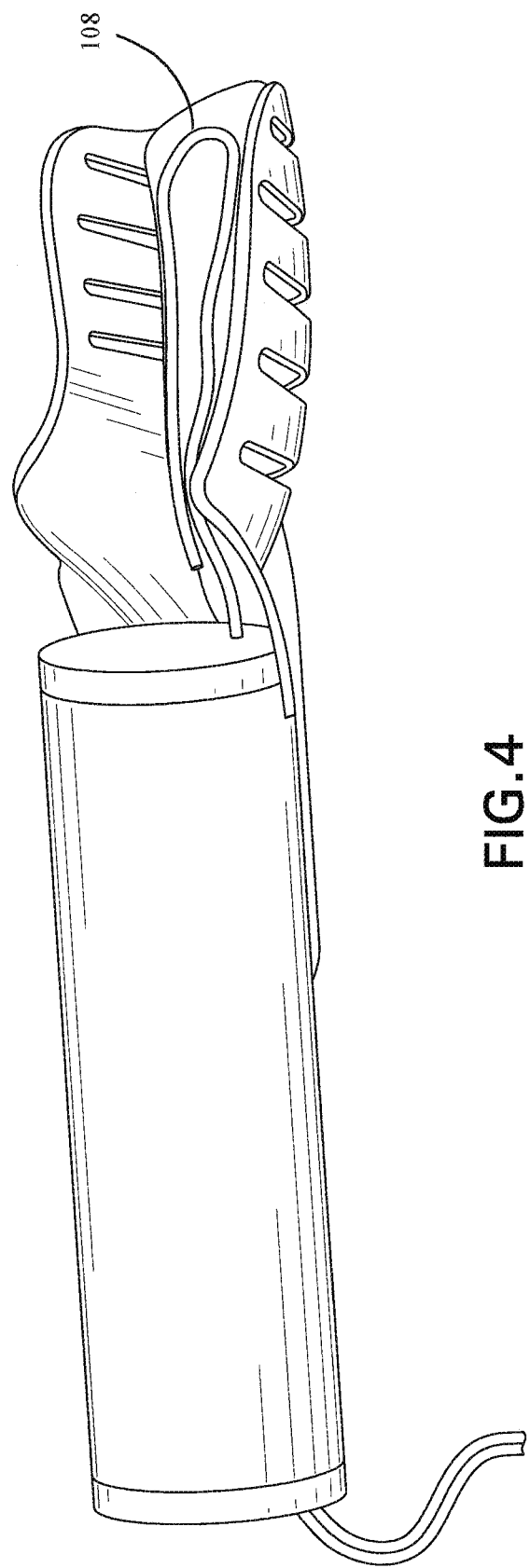
FIG. 4 is a side view of an alternative embodiment of the present invention.

Referring to FIG. 4, is a side view of an alternative embodiment of the present invention is provided for. Here, electrode 108 is shown by removing the top layer of insulation. By placing electrode 108 on top of the dental tray, a PEF will be generated around the area of a user's teeth while using the device.

Figure 5:
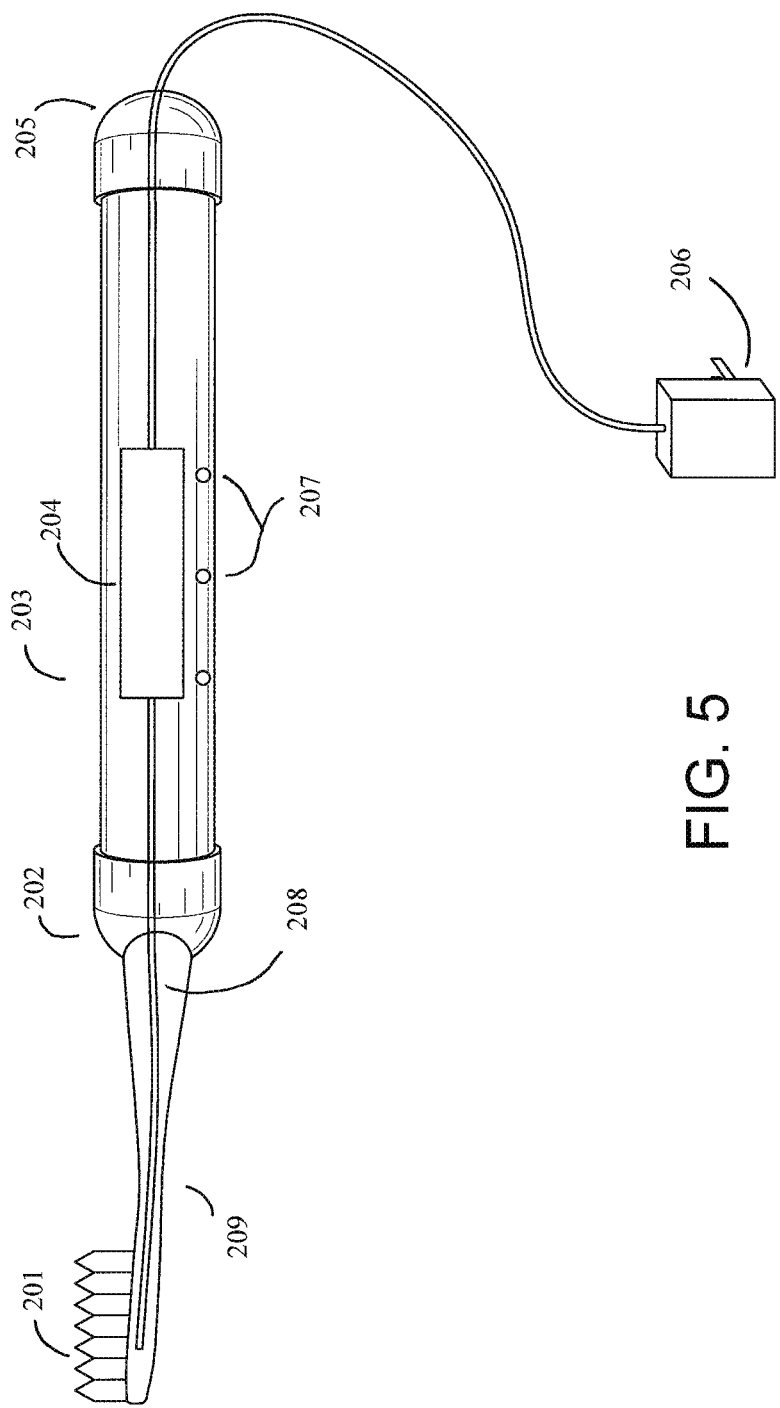
FIG. 5 is a side view of another embodiment of the present invention.

Referring to FIG. 5, a side view of an embodiment of the present invention incorporated into a toothbrush is shown. Specifically, toothbrush head 201 is connected to toothbrush base 209 to form an assembly. Toothbrush head 201 is readily replaceable and is capable of clicking into the toothbrush base 209. Toothbrush base 209 interfaces with first cap 202 which is attached to one end of handle 203. In a preferred embodiment, handle 203 is hollow and houses power supply 204. Power supply 204 is operatively connected to pipe 208. In another preferred embodiment, pipe 208 is rigid, insulated, and contains electrode 210 (See FIG. 6). Preferably, pipe 208 will have a very small diameter, to allow for greater ease of replacing toothbrush head 201 without damaging electrode 210 (See FIG. 6). The rigidity of pipe 208 also contributes to the ease of replacement of toothbrush head 201.

On the other end of handle 203 is second cap 205. In one embodiment, second cap 205 is equipped with a hole such that AC adapter 206 may be in electronic communication with a wall outlet and power supply 204. This embodiment is further equipped with cooling holes 207. In alternative embodiments, cooling holes 207 could be omitted and could be replaced with, for example a more efficient power supply 204, or a cooling fan. It should be noted that the present invention may be equipped with a dial that can have different settings. This dial may, for example, control the strength of the device (i.e. the voltage output) which may be of a high or low measurement with the exact measurement depending on the desired embodiment.

Figure 6:
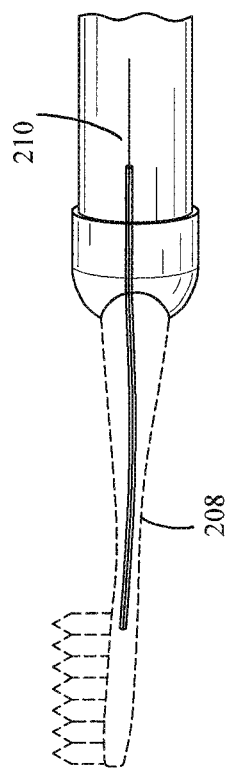
FIG. 6 is a side view of a cross-section of another embodiment of the present invention.

Referring to FIG. 6, a cross-sectional view of an embodiment of the present invention is provided for. This view highlights electrode 210 which is located at the center of pipe 208. Electrode 210 is in electric communication with power supply 204 (See FIG. 1). Power supply 204 (See FIG. 1) generates a PEF via electrode 210. In this particular embodiment the total length of the device will be around 19 cm. The length and size of the toothbrush base 209 will vary depending on the user's needs. The insulated handle 203 will be about 13 cm long with about a 2 cm diameter, which house the power supply 204. Further, if the cooling holes 207 are still needed they can be place anywhere on the handle but should be placed 1 cm away from each other. In another embodiment, the invention may be of varying lengths, widths, and sizes.

The device outlined is innovative in that it uses pulsed electric fields as a way to prevent biofilm growth and bacterial attachment as opposed to disinfection. Previous systems that have been made to effect dental plaque growth did not use a specific electric field to combat the growth of dental plaque, which is a form of biofilm. It is hypothesized that the device outlined, embodied in FIGS. 1-6 will reduce the bacterial growth and attachment in the mouth. The PEF treatment can also lead to electroporation causing the bacterial cell to die. As a result, reducing the concentration of biofilm formation. As the voltage strength increases the time needed to achieve the same result decreases and vice versa for lower voltage strengths.

This invention involves the application of electric field to a region above and/or surrounding a surface with the aim of preventing bacteria from attaching to the surface. A general design includes at least one high voltage electrodes thoroughly insulated with high voltage insulation such as glass, ceramic, or plastic insulation to prevent any sparking or current through the system. In other embodiments of the invention, other appropriate insulating material or materials may be used. The specific electrode geometry depends on the specific application and several examples are given here.

In an alternative embodiment of the present invention, electrical device 100 can be used in the processing of certain liquids such as juices or dairy products. The present invention has a variety of embodiment, each made at different sizes. This allows the present invention to be easily incorporated into any pre-existing manufacturing system. For example, a given food processing plant would merely have to replace their tubes with this embodiment of present invention. It should be noted that in other embodiments, the present invention may be comprised of a new wrap that may be retro-fitted to existing systems. This embodiment may be attached via friction, hook and loop fasteners, adhesives, and a number of other, not expressly listed mechanisms. This is intended to, for example, further simply the installation process as well as reduce the overall cost of implementation.

It may be used in other situations where preventing bacterial attachment to a surface is warranted.

In various embodiments, the present invention is not only applicable to permanently fixed object, but may be used to subject bacteria on a number of different surfaces to a PEF.

Preferably, the pulsing parameters for power supply 101 are between about 0.1 kV/cm and about 20 kV/cm and between about 5 kHz and about 60 kHz. However, it should be noted that in other embodiments, the power supply will have pulsing parameters between 0.1 kV/cm and 20 kV/cm. This provides for electric fields that are strong enough to disrupt the cells, but are not as high as those used for disinfection. A power source and the frequency ranges is chosen to reduce the cost of the device because the power sources cost less to make and the device is safer for public use. In a preferred embodiment, the pulsed electric field is not applied continuously. Rather, the power source is on for a short time and off for a much longer time, therefore reducing the duty cycle to increase efficiency. The choice of a specific duty cycle may be dependent on the doubling time for the bacterial species targeted.

The device outlined is innovative in that it uses pulsed electric fields as a way to prevent biofilm growth and bacterial attachment as opposed to disinfection.

Figure 7:
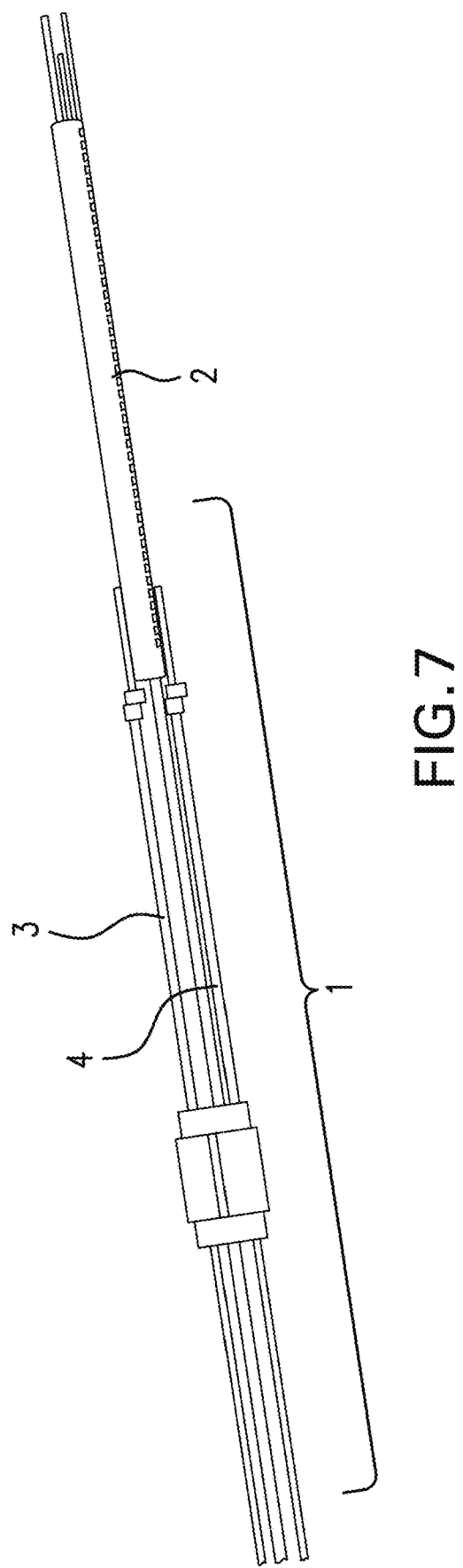
FIG. 7 is a perspective view shows a possible surface to high voltage connector layout.
Figure 8:
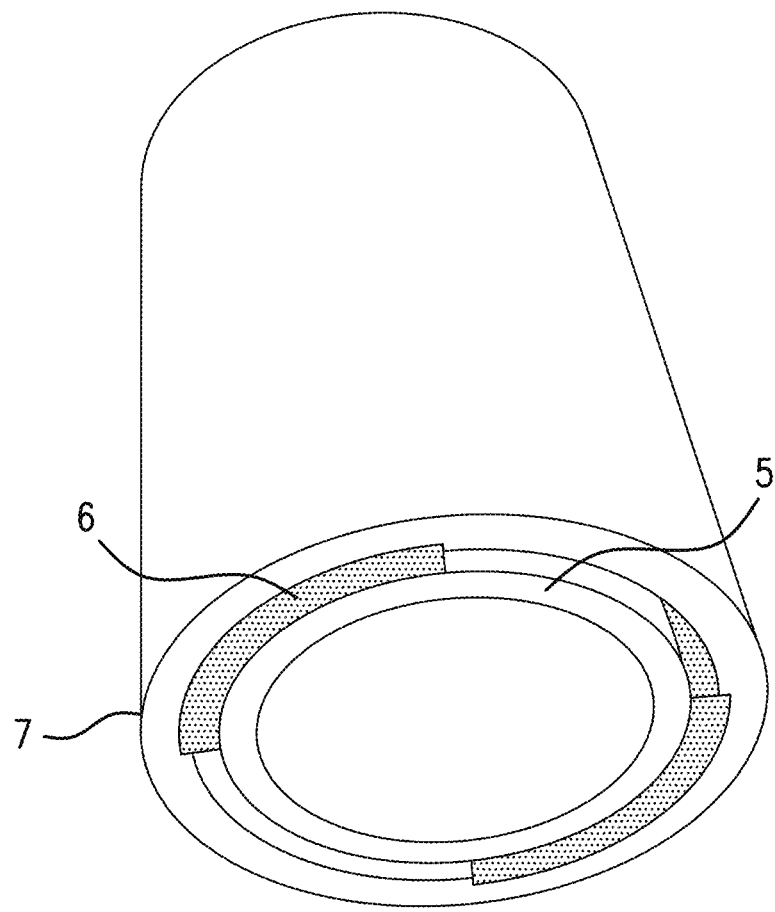
FIG. 8 is a perspective view of a possible surface layout of an embodiment of the present invention.

Referring to FIG. 7 and FIG. 8, tubing 2 is used. Surfaces, an example of such is tubing 5, will have two electrodes 6 applied to the surface 5. The electrodes 6 are attached to a high voltage connector 1; one of the electrodes is attached to the high voltage wire 3 from the connector and the other electrode is attached to the neutral wire from the connector 4. This connector will be attached into a high voltage high frequency power supply. All electrodes 6 are insulated 7. In an alternative embodiment, the present invention will be comprised of high voltage wire 3, and a negative voltage wire in lieu of the neutral wire. In another embodiment, the invention may be a complex, multifaceted piece such as a fitting or a joint.

A possible use of the sample invention in FIG. 7 is in the processing of certain liquids such as juices or dairy products. The invention can be made at variable sizes, so it can be easily incorporated into any pre-existing manufacturing system. A processing plant would simply have to replace their tubes with this present invention (or attach our wrap electrodes), provide an electrical source for the power supply, and then let the system run. Although the preceding description of the present invention contains significant details, it should not be construed as the limiting scope of the invention but rather as possible application of the invention. It may be used in other situations where preventing bacterial attachment to a surface is warranted.

Figure 9:
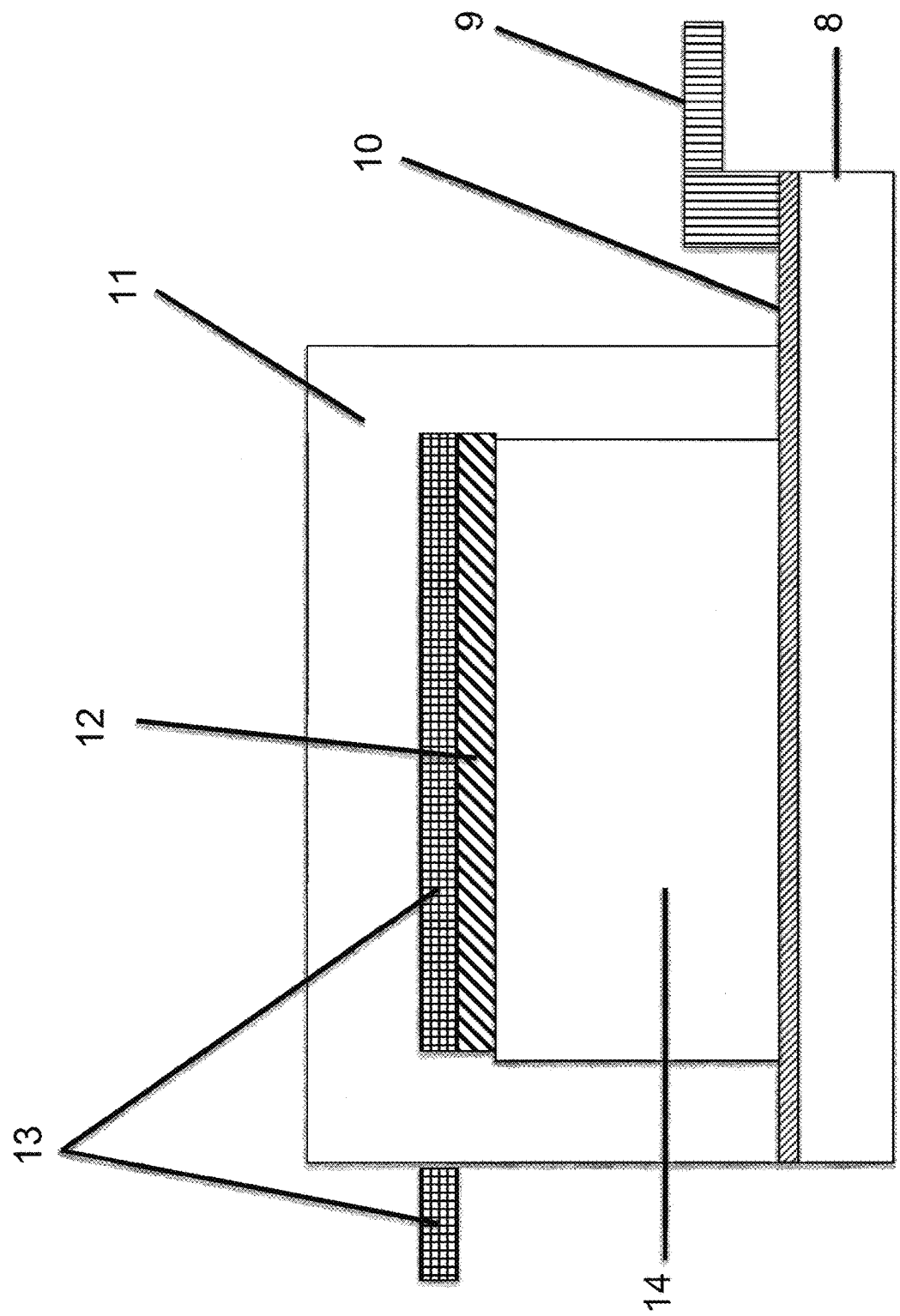
FIG. 9 is a side view of an electric field treatment chamber.

The invention is not only applicable to permanently fixed objects. Surface disinfection can apply to many surfaces. FIG. 9 shows another method of applying the electric fields used for prevention of biofilm growth and/or bacterial contamination. An insulating base 8 and structure 11 can be used to hold electrodes. An electrode 10 is grounded 9 while another electrode 13 has the high voltage applied to it. This high voltage electrode 13 is insulated 12. In another embodiment, the ground may be substituted for a positive electrode or an electrode with a different voltage than the high voltage electrode 13. The space between the two electrodes is the "treatment chamber" 14. This set-up FIG. 9 is applicable to, but not limited to, such objects as dentures. Continuing with the example of dentures, when they are not in use they can have biofilm growing or bacterial infecting them; this is when the present invention will be used to prevent this bacterial growth.

Figure 10:
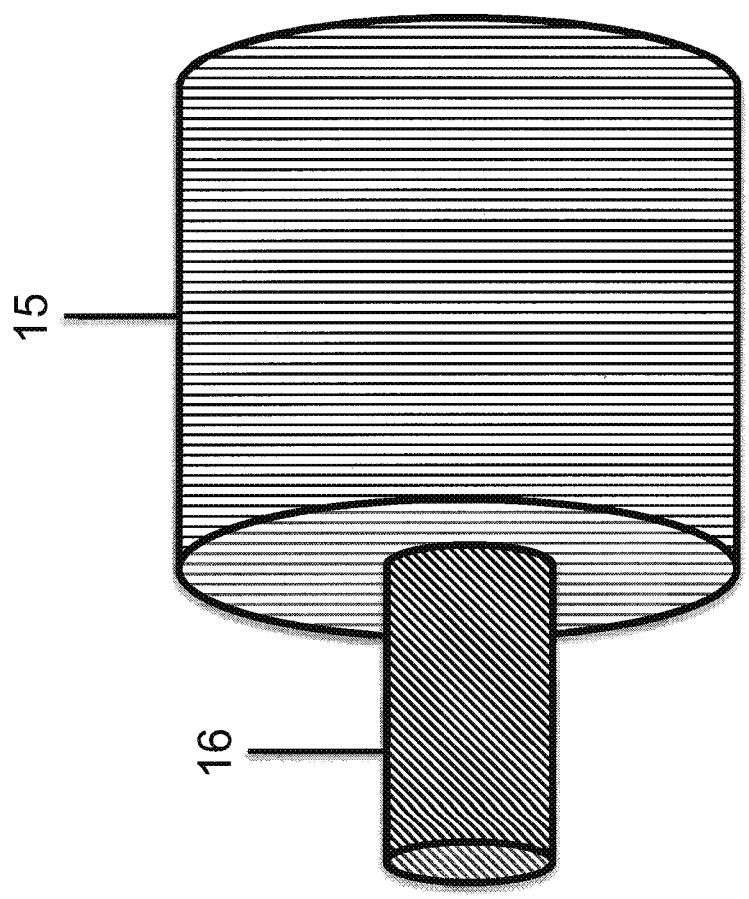
FIG. 10 is a perspective view of a single electrode embodiment of the present invention.

FIG. 10 shows a possible single electrode design. A high voltage electrode 16 is insulated 15 to prevent current leakage and to ensure safety of the product. Examples of applications of such as design include but are not limited to electric field treatment of teeth, medical tools, and implants.

Figure 11:
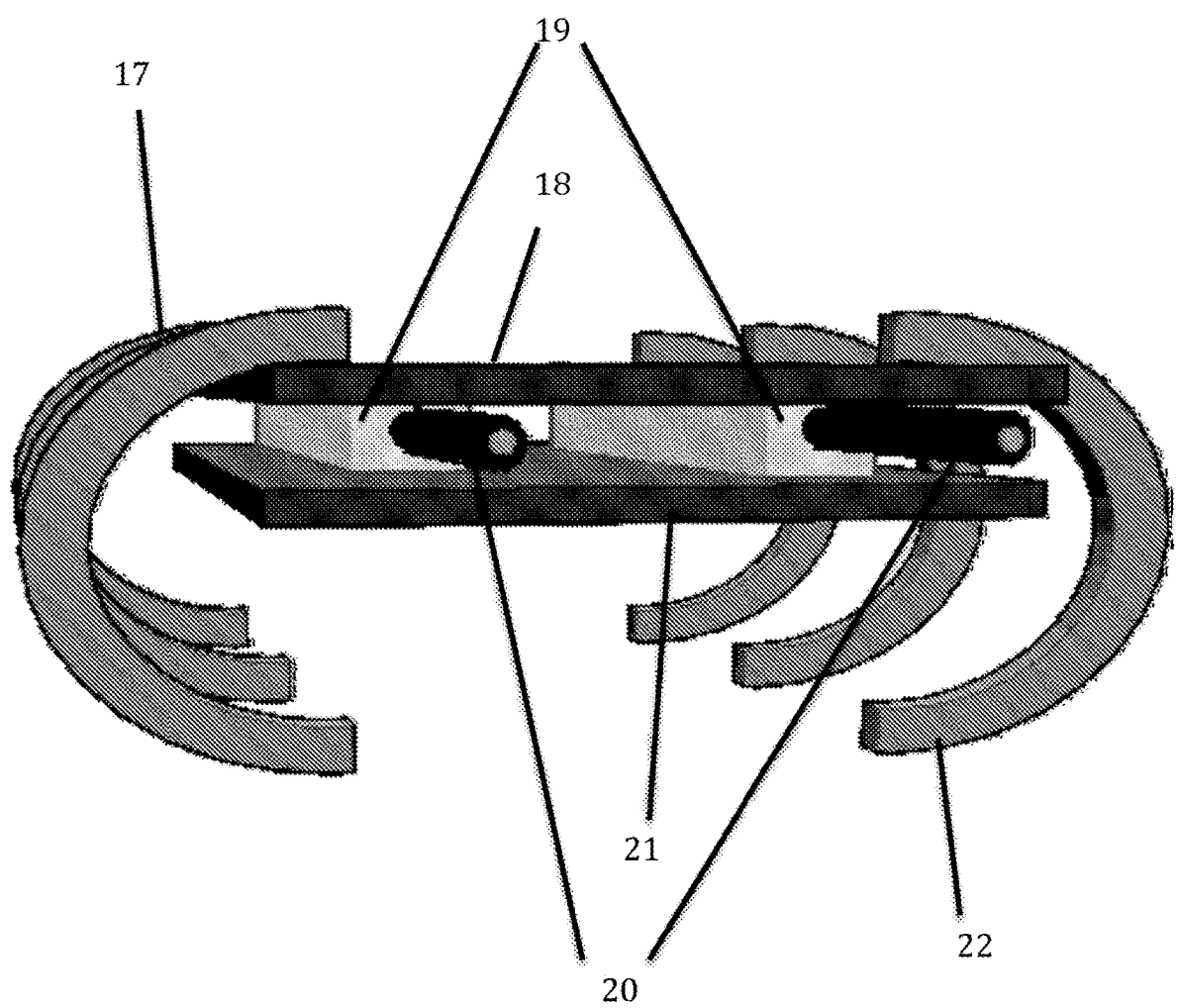
FIG. 11 is a perspective view of a possible electrode wrap design.

Referring to FIG. 11, left wrap adhesive 17 attaches to right adhesive 22 when inner insulation 21 is curled around a given surface 5. A plurality of adhesives 17 and 22 can be used to secure one end of the wrap around the tube to another end. One of either the left wrap adhesive 17 or right wrap adhesive 22 can be eliminated if one is sufficient to attach the wrap design to a surface. Any number of electrodes 20 can be insulated by any number of insulators 19. These insulated electrodes may be positioned between the inner wrap 21 and outer wrap 18. In some instances, the inner wrap 21 and outer wrap 18 may provide insulative properties thereby removing the need for the insulators 19.

Overall wrap design, represented in FIG. 11, can be an apparatus that is cylindrical, rectangular, or any combination of shapes and sizes. Electrodes 20 can be separated at a distance so that electric field is created between the two. Electrodes 20 may be parallel when wrapped around a cylindrical surface, but this is not necessary. Separation distance between electrodes 20, and therefore widths of insulators 19 and 20, can be made larger to accommodate larger circumference surfaces. For example, if the surface to be treated is the inside of a tube with inner diameter of ⅞ inch and outer diameter of 1 inch, then a wrap of over 6.28 (2 pi) inches width can have the centers of their electrodes 3.14 (pi) apart so that they are parallel. This is meant for example only as the dimensions can vary.

The device outlined is innovative in that it uses pulsed electric fields as a way to prevent biofilm growth and bacterial attachment as opposed to disinfection. Previous systems have been made where higher voltage electric fields were used to kill bacteria, but our product is not designed to kill. It is hypothesized that the device outlined, embodied in FIGS. 7, 8, and 11, will reduce bacterial attachment to inside of surface 5. This effect can also be caused to surfaces in treatment chamber 14 or near electrode 16. The PEF treatment, in addition to reducing cells ability to attach to surfaces, are hypothesized to also reduce cells abilities to reproduce, theoretically reducing or preventing growth in bacterial population size. If electroporation is caused due to device outlines, cell death or harm may also occur, further reducing bacterial reproduction.

In a preferred embodiment, the present invention is comprised of an electrode surrounded by an insulator to produce an electric field without having the risk of current flowing through the human mouth. In one embodiment, a small neon transformer is powering the invention. In a preferred embodiment, the aforementioned electrode is constructed out of copper. This is because of its low resistance. In another preferred embodiment, the present invention will have a handle that is comprised of a ceramic tube, further insulated by a rubber coating. In another preferred embodiment, the present invention will be equipped with at least one vent to provide for airflow. However, once the invention is manufactured the vents can be replaced with a cooling fan or with a power supply with a better heat sink. Further, the handle and the base of the toothbrush will be insulated. This ensures that little or no current will flow from the handle, or the mouthpiece, to the user. Further, having a ridged, insulated pipe feature allows the toothbrush head to be changed safely without disrupting the electrode, all without having to replace the entirety of the toothbrush. In a yet another preferred embodiment, this insulated electrode for removing biofilm from one's mouth will be combined with a standard toothbrush or an electric toothbrush.

In another embodiment, the area of the electrode that will be placed in a human mouth employs an insulated spiraling copper wire sealed with medical-grade epoxy, placed between two ceramic pieces, and is then subsequently encapsulated by a small ridge, preferably constructed out of a food-grade rubber.

In another embodiment the toothbrush or dental tray may include a power switch or an on/off switch. In yet another embodiment the toothbrush or dental tray may include a dial for regulating voltage to adhere to a user's age or tolerance level. In another embodiment, the electrical field generator may comprise an elongated device that is configured and safe for insertion into a user's mouth. In another embodiment, the toothbrush of dental tray may utilize alternative power supply which reduces heat. In such an embodiment, the air vents may be closed or are smaller in size. In another embodiment, the toothbrush may be powered and include a vibrating or oscillating toothbrush head. In yet another embodiment, the toothbrush may be include a charging deck or station and is DC powered. In another embodiment, the toothbrush may include a timer with configurable time intervals. In another embodiment, the toothbrush may be configured and adapted for use on animals. In another embodiment, the AC adapter of the toothbrush may be removable from the base.

In another embodiment, the electrodes may be comprised of platinum or like elements. In yet another embodiment, biofilm on dentures may be treated with electrical field generation wherein the treatment chamber is comprised of denture container surrounded by electrodes. In yet another embodiment, biofilm on teeth may be treated with electrical field generation wherein the treatment chamber is comprised of a dental mouth tray. In yet another embodiment, biofilm on medical instruments may be treated with electrical field generation wherein the treatment chamber is comprised of an incubator comprised of electrodes. In yet another embodiment, biofilm on contact lenses may be treated with electrical field generation wherein the treatment chamber is comprised of a contact lens container surrounded by electrodes. In yet another embodiment, biofilm on tracheal tubes, medical and dental implants and food and liquids may be treated with electrical field generation wherein the treatment chamber is comprised of tubing surrounded by electrodes.

The many elements of the present invention make it unique in the field. Although this invention has been described with a certain degree of particularity, it is to be understood that the present disclosure has been made only by way of illustration and that numerous changes in the details of construction and arrangement of parts may be resorted to without departing from the spirit and the scope of the invention.

Various other components may be included and called upon for providing for aspects of the teachings herein. For example, additional materials, combinations of materials and/or omission of materials may be used to provide for added embodiments that are within the scope of the teachings herein. In the present application a variety of variables are described, including but not limited to components and conditions. It is to be understood that any combination of any of these variables can define an embodiment of the disclosure. Other combinations of articles, components, conditions, and/or methods can also be specifically selected from among variables listed herein to define other embodiments, as would be apparent to those of ordinary skill in the art.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof. Therefore, it is intended that the disclosure not be limited to the particular embodiments disclosed.

What is claimed:

1. A method of inhibiting biofilm growth on a substrate, comprising the steps of:
    coating, said substrate with a conductive polymer;
    generating, a pulsed electric field with an intensity of at least 400V/cm;
    exposing, for a period of time, said substrate to said pulsed electric field, wherein said period of time is at least one second.

2. The method of claim 1, wherein the substrate comprises an inside surface of closed tubing in food processing plants, medical equipment, medical tubing, implants, dental implants, teeth, or toothbrush filaments.

3. The method of claim 1, wherein the pulsed electric field has an intensity of less than 2000V/cm.

4. The method of claim 1, wherein the method further comprises inhibiting bacterial attachment to a surface of the conductive polymer.

5. The method of claim 1, wherein the pulsed electric field is generated by an electrode.

6. The method of claim 5, wherein the electrode is completely insulated.

7. The method of claim 5, wherein the electrode is constructed out of copper.

8. The method of claim 1, wherein the substrate is used in the food industry.

9. The method of claim 1, wherein the pulsed electric field is generated by using AC power.

10. The method of claim 1, wherein the pulsed electric field is generated by using DC power.

11. The method of claim 1, wherein the pulsed electric field is generated by an electric field generator, the electric field generator comprising a power source, having an output;
    an alternating current (AC) adapter coupled to said power source and configured to send AC power through said output; a first fully insulated electrode connected to said output of said power source, wherein the first electrode is enclosed in an insulation that prevents current flowing from the first electrode; an insulated handle; and ground, wherein said first insulation enclosed electrode and said ground are situated such that an electric field is generated in the space between said first electrode and said ground, and wherein said electric field has an intensity ranging from about 400V/cm to about 20 kV/cm.

12. The method of claim 11, wherein the ground is comprised of a second fully insulated electrode with an opposite voltage of the first electrode, wherein the second electrode is enclosed in an insulation that prevents current flowing from the second electrode.

13. The method of claim 11, wherein the ground is comprised of at least a plurality of fully insulated electrodes, wherein the plurality of electrodes are fully insulated with an insulation that prevents current flowing from the plurality of electrodes.

* * * * *